United States Patent
Setamou et al.

(10) Patent No.: US 10,143,197 B1
(45) Date of Patent: Dec. 4, 2018

(54) INSECT ATTRACTANTS

(71) Applicants: Mamoudou Setamou, Weslaco, TX (US); Darek Czokajlo, West Linn, OR (US); Robert Saldana, Weslaco, TX (US)

(72) Inventors: Mamoudou Setamou, Weslaco, TX (US); Darek Czokajlo, West Linn, OR (US); Robert Saldana, Weslaco, TX (US)

(*) Notice: Subject to any disclaimer, the term of this patent is extended or adjusted under 35 U.S.C. 154(b) by 0 days.

(21) Appl. No.: 15/648,208

(22) Filed: Jul. 12, 2017

(51) Int. Cl.
*A01N 27/00* (2006.01)
*A01N 31/02* (2006.01)

(52) U.S. Cl.
CPC ............ *A01N 27/00* (2013.01); *A01N 31/02* (2013.01)

(58) Field of Classification Search
None
See application file for complete search history.

(56) References Cited

U.S. PATENT DOCUMENTS

2005/0074509 A1* 4/2005 Belloni Regazzo ... A61K 36/22 424/769
2017/0367386 A1* 12/2017 McElvany .............. A23L 27/12

* cited by examiner

*Primary Examiner* — Robert A Wax
*Assistant Examiner* — Melissa S Mercier
(74) *Attorney, Agent, or Firm* — Mohr Intellectual Property Law Solutions, PC

(57) ABSTRACT

An insect attractant including a blend of volatile organic compounds. The blend of volatile organic compounds may include alpha-phellandrene, beta-caryophyllene, and at least one additional volatile organic compound. In one embodiment, the ratio of alpha-phellandrene to beta-caryophyllene in the blend may be 1:0.5 to 1:2. In one embodiment, the blend of volatile organic compounds may comprise 15 to 60 wt. 0% alpha-phellandrene and 10 to 50 wt. % beta-caryophyllene. In one embodiment, the at least one additional volatile organic compound may be selected from the group consisting of: beta-phellandrene, gamma-terpinene, ocimene, and terpineol.

13 Claims, 6 Drawing Sheets

| MS1 | |
|---|---|
| Component | wt. % |
| alpha-phellandrene | 55% |
| beta-caryophyllene | 45% |

| MS1a | |
|---|---|
| Component | wt. % |
| alpha-phellandrene | 36% |
| beta-caryophyllene | 29% |
| linalool | 13% |
| citral | 9% |
| gamma-terpinene | 13% |

| MS1d | |
|---|---|
| Component | wt. % |
| alpha-phellandrene | 35% |
| beta-caryophyllene | 28% |
| linalool | 13% |
| citral | 9% |
| gamma-terpinene | 13% |
| palmitic acid | 0.2% |
| linoleic acid | 0.2% |
| beta-sitosterol | 0.5% |
| Hexacosanol | 1.0% |
| Heneicosane | 1.0% |

| MS1L | |
|---|---|
| Component | wt. % |
| alpha-phellandrene | 55% |
| beta-caryophyllene | 45% |
| methyl salicylate | 0.01% |

| MS1b | |
|---|---|
| Component | wt. % |
| alpha-phellandrene | 36% |
| beta-caryophyllene | 29% |
| linalool | 13% |
| citral | 9% |
| gamma-terpinene | 13% |
| palmitic acid | 0.3% |
| linoleic acid | 0.3% |

| MS1g | |
|---|---|
| Component | wt. % |
| alpha-phellandrene | 55% |
| beta-caryophyllene | 45% |
| Gamma-butyrolactone | 0.5% |

| MS1CO | |
|---|---|
| Component | wt. % |
| alpha-phellandrene | 28% |
| beta-caryophyllene | 23% |
| clove oil | 50% |

| MS1HC | |
|---|---|
| Component | wt. % |
| alpha-phellandrene | 55% |
| beta-caryophyllene | 45% |
| dodecanoic acid | 0.05% |
| heptacosane | 0.05% |

| MS1 | |
|---|---|
| Component | wt. % |
| alpha-phellandrene | 55% |
| beta-caryophyllene | 45% |

| MS1a | |
|---|---|
| Component | wt. % |
| alpha-phellandrene | 36% |
| beta-caryophyllene | 29% |
| linalool | 13% |
| citral | 9% |
| gamma-terpinene | 13% |

| MS1d | |
|---|---|
| Component | wt. % |
| alpha-phellandrene | 35% |
| beta-caryophyllene | 28% |
| linalool | 13% |
| citral | 9% |
| gamma-terpinene | 13% |
| palmitic acid | 0.2% |
| linoleic acid | 0.2% |
| beta-sitosterol | 0.5% |
| Hexacosanol | 1.0% |
| Heneicosane | 1.0% |

| MS1L | |
|---|---|
| Component | wt. % |
| alpha-phellandrene | 55% |
| beta-caryophyllene | 45% |
| methyl salicylate | 0.01% |

| MS1b | |
|---|---|
| Component | wt. % |
| alpha-phellandrene | 36% |
| beta-caryophyllene | 29% |
| linalool | 13% |
| citral | 9% |
| gamma-terpinene | 13% |
| palmitic acid | 0.3% |
| linoleic acid | 0.3% |

| MS1g | |
|---|---|
| Component | wt. % |
| alpha-phellandrene | 55% |
| beta-caryophyllene | 45% |
| Gamma-butyrolactone | 0.5% |

| MS1CO | |
|---|---|
| Component | wt. % |
| alpha-phellandrene | 28% |
| beta-caryophyllene | 23% |
| clove oil | 50% |

| MS1HC | |
|---|---|
| Component | wt. % |
| alpha-phellandrene | 55% |
| beta-caryophyllene | 45% |
| dodecanoic acid | 0.05% |
| heptacosane | 0.05% |

Fig. 1

| MS1aL | |
|---|---|
| Component | wt. % |
| alpha-phellandrene | 36% |
| beta-caryophyllene | 29% |
| linalool | 13% |
| citral | 9% |
| gamma-terpinene | 13% |
| methyl salicylate | 0.01% |

| MS1aL+ | |
|---|---|
| Component | wt. % |
| alpha-phellandrene | 35% |
| beta-caryophyllene | 29% |
| linalool | 13% |
| citral | 9% |
| gamma-terpinene | 13% |
| Hexacosanol | 0.5% |
| Heneicosane | 0.5% |
| methyl salicylate | 0.01% |

| MS1-b-CO-HC-L 1 part | |
|---|---|
| Component | wt. % |
| alpha-phellandrene | 18% |
| beta-caryophyllene | 15% |
| linalool | 6% |
| citral | 4% |
| gamma-terpinene | 6% |
| palmitic acid | 0.3% |
| linoleic acid | 0.3% |
| Clove oil | 50% |
| Dodecanoic acid | 0.3% |
| Heptacosene | 0.05% |
| Methyl salicylate | 0.01% |

| MS1-b-CO-HC-L 2 part | |
|---|---|
| Component | wt. % |
| alpha-phellandrene | 18% |
| beta-caryophyllene | 15% |
| linalool | 6% |
| citral | 4% |
| gamma-terpinene | 6% |
| Clove oil | 50% |
| Methyl salicylate | 0.01% |
| Dodecanoic acid | 0.3% |
| Heptacosene | 0.3% |
| palmitic acid | 0.05% |
| linoleic acid | 0.3% |

INSECT ATTRACTANTS

BACKGROUND

The present disclosure relates generally to chemical insect attractants. In particular, chemical insect attractants effective to attract the Asian citrus psyllid, known as *D. citri*, are described.

The Asian citrus psyllid, *Diaphorina citri* (*D. citri*), vectors three phloem-restricted bacteria in the genus *Candidatus Liberibacter*, which have been associated with huanglongbing (HLB), otherwise known as citrus greening disease. Citrus trees infected by HLB produce small, misshapen fruit characterized by bitter taste, rendering the juice and related products unmarketable. Infected trees gradually decline, drop much of their fruit load and ultimately die.

*D. citri* was first reported in Florida in 1998, but has invaded many more regions, which include all citrus growing areas of the continental U.S., Puerto Rico and Hawaii. HLB was first discovered in Florida in 2005 and is now well-established. It has been confirmed in several commercial groves in Texas and in only one residential tree in California. Whereas the psyllid has been detected in several areas in Arizona, neither psyllids nor plant material has tested positive for *Liberibacter*.

Current sampling protocols for adult *D. citri* rely on passive sticky traps, which capture *D. citri* by incidental or random encounters of flying adults with these sticky surfaces or by tap sampling in which tree branches are shaken to dislodge psyllids onto a sticky surface held below the branch. This renders adult psyllid monitoring for forecasting or evaluating insecticide applications inaccurate.

Currently, a semiochemical-based lure (chemical used for communication between individuals) to attract *D. citri* is not commercially available. *D. citri* exhibits strong preference for citrus volatiles and aggregate and lays eggs exclusively on young unexpanded leaves. Thus, plant-related chemicals are crucial signals used by adults for plant selection. In addition, there is evidence documenting that mate location in *D. citri* is mediated by a volatile sex pheromone and hydrocarbons emitted from the cuticle or outer surface of the insect.

Thus, there exists a need for *D. citri* chemical attractants that improve upon and advance the state of the art. Examples of new and useful chemical insect attractants relevant to the needs existing in the field are discussed below.

An insect attractant may comprise a blend of volatile organic compounds. The blend of volatile organic compounds may comprise alpha-phellandrene, beta-caryophyllene, and at least one additional volatile organic compound. In one embodiment, the ratio of alpha-phellandrene to beta-caryophyllene in the blend may be 1:0.5 to 1:2. In one embodiment, the blend of volatile organic compounds may comprise 15 to 60 wt. % alpha-phellandrene and 10 to 50 wt. % beta-caryophyllene. In one embodiment, the at least one additional volatile organic compound may be selected from the group consisting of: beta-phellandrene, gamma-terpinene, ocimene, and terpineol.

SUMMARY

An insect attractant may comprise a blend of volatile organic compounds. The blend of volatile organic compounds may comprise alpha-phellandrene, beta-caryophyllene, and at least one additional volatile organic compound. In one embodiment, the ratio of alpha-phellandrene to beta-caryophyllene in the blend may be 1:0.5 to 1:2.

In another embodiment, the ratio of alpha-phellandrene to beta-caryophyllene in the blend may be 1:0.6 to 1:1.5. In another embodiment, the ratio of alpha-phellandrene to beta-caryophyllene in the blend may be 1:0.7 to 1:1.

In one embodiment, the blend of volatile organic compounds may comprise 15 to 60 wt. % alpha-phellandrene and 10 to 50 wt. % beta-caryophyllene. In another embodiment, the blend of volatile organic compounds may comprise 20 to 50 wt. % alpha-phellandrene and 15 to 40 wt. % beta-caryophyllene. In another embodiment, the blend of volatile organic compounds may comprise 25 to 50 wt. % alpha-phellandrene and 20 to 30 wt. % beta-caryophyllene.

In one embodiment, the at least one additional volatile organic compound may be selected from the group consisting of: beta-phellandrene, gamma-terpinene, ocimene, and terpineol.

In some embodiments, the at least one additional volatile organic compound includes gamma-terpinene. For example, the blend of volatile organic compounds may comprise at least 5 wt. % gamma-terpinene. In another example, the blend of volatile organic compounds may comprise at least 10 wt. % gamma-terpinene. In yet another example, the blend of volatile organic compounds may comprise 5 to 15 wt. % gamma-terpinene.

In some embodiments, the at least one additional volatile organic compound includes beta-phellandrene. For example, the blend of volatile organic compounds may comprise at least 30 wt. % beta-phellandrene.

In some embodiments, the at least one additional volatile organic compound includes linalool. For example, the blend of volatile organic compounds may comprise at least 5 wt. % linalool. In another example, the blend of volatile organic compounds may comprise at least 10 wt. % linalool. In yet another example the blend of volatile organic compounds may comprise at 5 to 15 wt. % linalool.

BRIEF DESCRIPTION OF THE DRAWINGS

FIG. 1 shows the compositions of a first set of insect attractant blends of volatile organic compounds.

FIG. 2 shows the compositions of a second set of insect attractant blends of volatile organic compounds.

DETAILED DESCRIPTION

Figure 3:
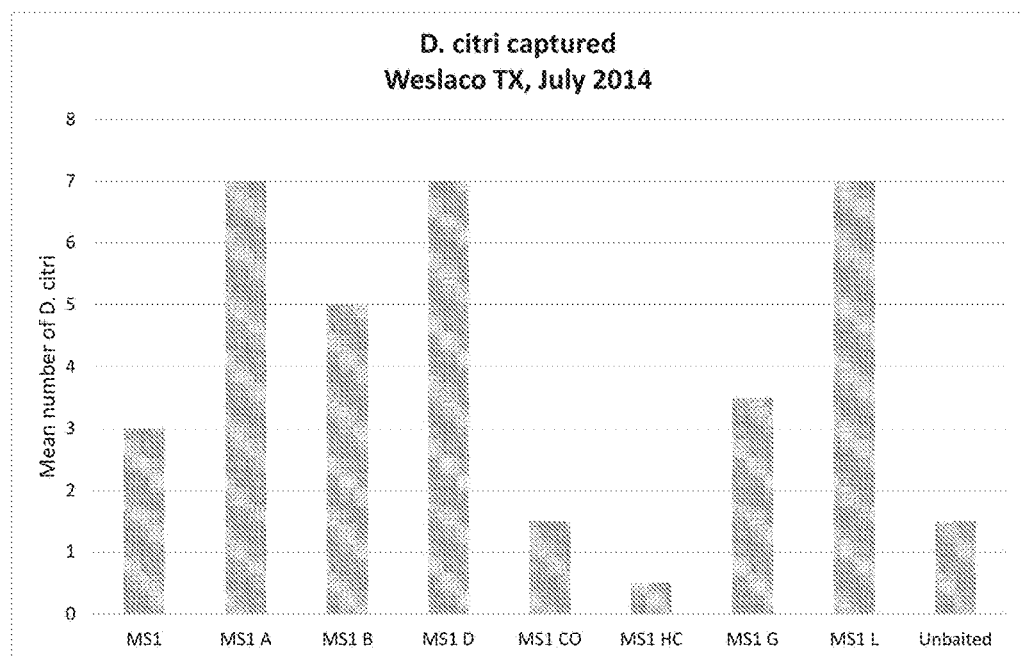
FIG. 3 is a bar graph showing mean numbers of *D. citri* individuals captured via each of several insect attractant blends during a first experiment.
Figure 4:
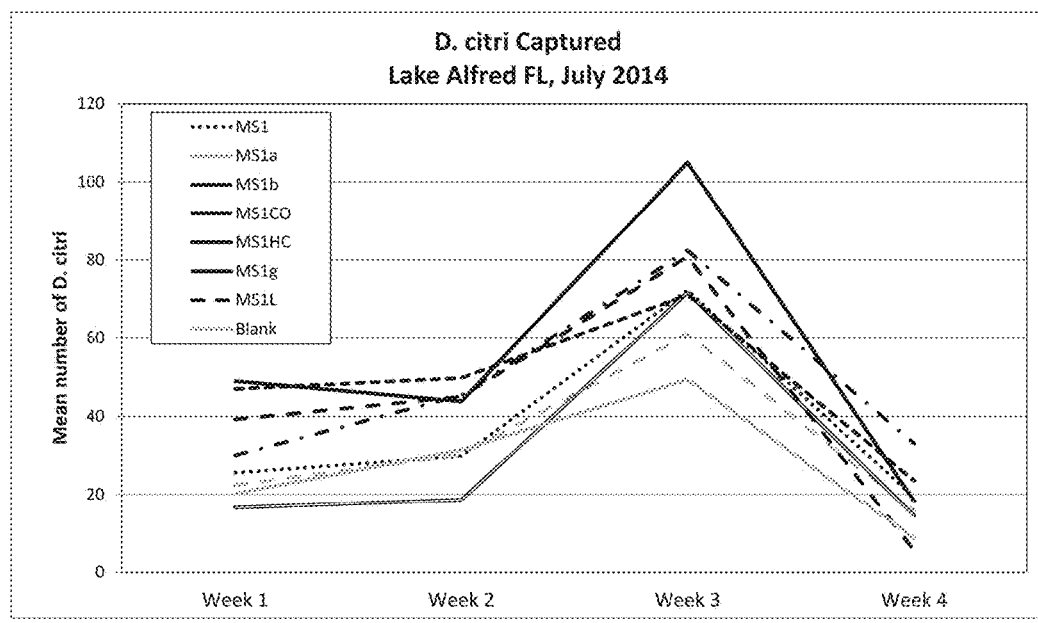
FIG. 4 is a line graph showing mean numbers of *D. citri* individuals captured via each of several insect attractant blends during the first experiment.
Figure 5:
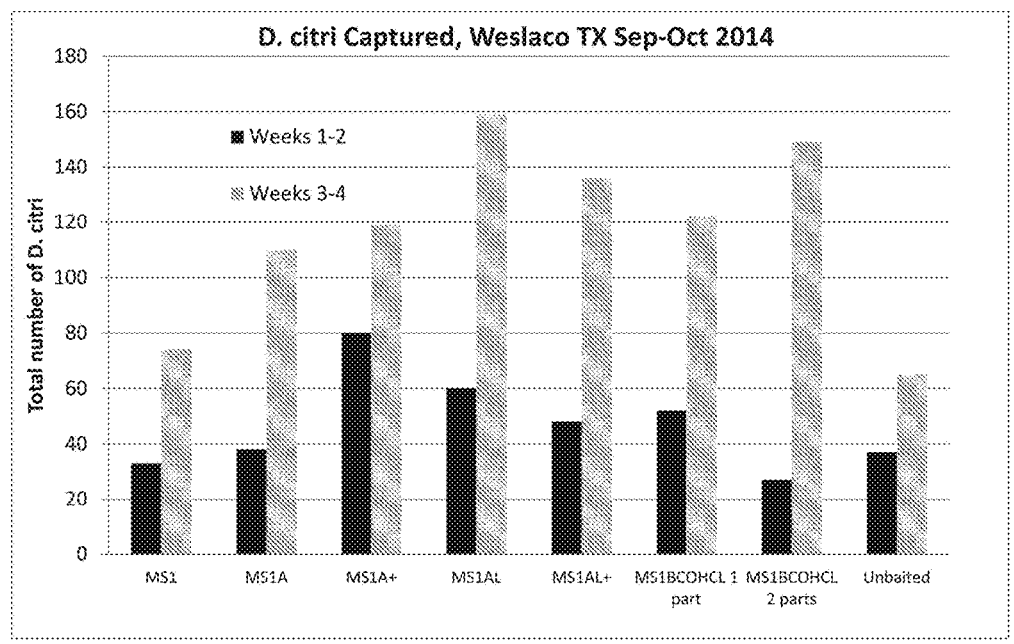
FIG. 5 is a bar graph showing mean numbers of *D. citri* individuals captured via each of several insect attractant blends during a second experiment.
Figure 6:
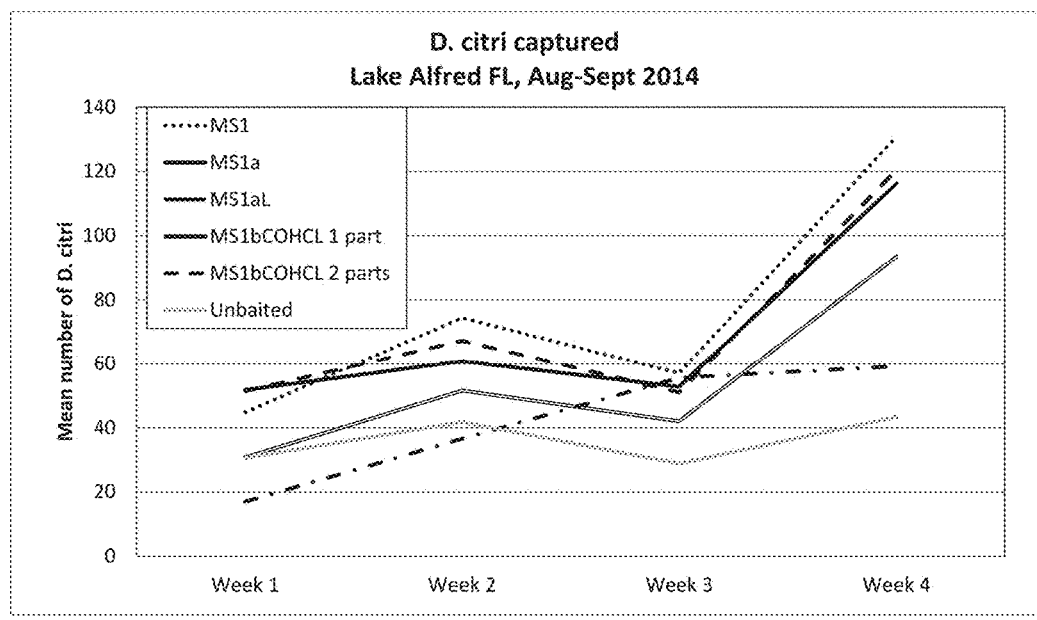
FIG. 6 is a line graph showing mean numbers of *D. citri* individuals captured via each of several insect attractant blends during the second experiment.

The disclosed insect attractants will become better understood through review of the following detailed description in conjunction with the figures. The detailed description and figures provide merely examples of the various inventions described herein. Those skilled in the art will understand that the disclosed examples may be varied, modified, and altered without departing from the scope of the inventions described herein. Many variations are contemplated for different applications and design considerations; however, for the sake of brevity, each and every contemplated variation is not individually described in the following detailed description.

Throughout the following detailed description, examples of various insect attractants are provided. Related features in the examples may be identical, similar, or dissimilar in different examples. For the sake of brevity; related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portrayal of a related feature in any given figure or example.

Eight different species of plants known to be *D. citri* host plants were obtained. Samples of air-entrained volatile compounds from intact, newly-emerged flush shoots were collected from each of the plants. Each sample was then analyzed via gas-chromatograph mass spectroscopy to determine the chemical composition of the samples. From the dozens of compounds identified, the following six volatile compounds were selected as potential semiochemicals for the insect attractant blends: alpha-phellandrene, beta-phellandrene, beta-caryophyllene, gamma-terpinene; ocimene; terpineol.

Experiments in the field were conducted on various blends and ratios of the above six volatile compounds, in addition to number of additional compounds, were conducted. Through these experiments, particularly efficacious blends and ratio of the compounds were identified.

For example, in some embodiments, the blend includes alpha-phellandrene, beta-phellandrene and beta-caryophyllene. In some embodiments, the ratio of alpha-phellandrene: beta-phellandrene:beta-caryophyllene in the blend of volatile organic compounds is in the range of 1-2:1-2:1-2. In other embodiments, the blend includes alpha-phellandrene, beta-phellandrene, beta-caryophyllene, gamma-terpinene, and ocimene. In some embodiments, the ratio of alpha-phellandrene:beta-phellandrene:beta-caryophyllene: gamma-terpinene:ocimene in the blend of volatile organic compounds is in the range of 3-5:3-5:2-3:1-2:1-2. In still other embodiments, the blend includes alpha-phellandrene, beta-phellandrene, beta-caryophyllene, gamma-terpinene, ocimene, terpineol. In some embodiments the ratio of alpha-phellandrene:beta-phellandrene:beta-caryophyllene: gamma-terpinene:ocimene:terpineol in the blend of volatile organic compounds is in the range of 3-5:3-5:3-4:1-3:1-2: 1-2.

To test the potential semiochemicals for their ability to attract adult *D. citri*, the number of *D. citri* captured on baited green-colored traps was compared to those captured on non-baited green-colored traps. Traps were placed on the outer canopy of citrus trees at five feet above the ground along the edge of all four sides of groves. Trees were spaced about 24 feet apart, only one trap per tree. Formulations of active compounds were placed directly on traps in a controlled release device. All treatments were replicated eight times at two different sites in Florida and Texas. In Florida, the lures were tested in Valencia and Hamlin orange groves. In Texas, evaluations were conducted in lemon groves.

There were two experiments. In Experiment One, blends were tested in June and July 2014; and in Experiment Two, blends were tested in August through October 2014.

Experiment 1

For Experiment One, a first set of different blends was formulated. The blends of the first set were designated as MS1, MS1a, MS1b, MS1d, MS1CO, MS1HC, MS1g, MS1L. In addition to the host-plant volatiles discussed above, some of the blends included volatiles produced by the *D. citri*. Specifically, five blends included host-plant volatiles only, and three blends included *D. citri*-produced compounds in addition to plant volatiles. The compositions of these blends are shown in FIG. 1. All eight blends were tested in Texas, and seven blends were tested in Florida. Traps baited with the blends were checked and replaced weekly, and the number of *D. citri* captured on traps was counted. Results of Experiment One are shown in FIGS. 3-4.

Experiment 2

Based on results from Experiment One, a second set of seven blends of volatiles was produced for Experiment Two. The blends of the second set were designated as MS1, MS1a, MS1a+, MS1aL, MS1aL+, MS1BCOHCL 1 part and MS1BCOHCL 2 part. The compositions of MS1, and MS1a in the second set were the same as in the first set of blends. The compositions of the new blends of the second set are shown in FIG. 2. Again, some of the blends included volatiles produced by the *D. citri* in addition to plant volatiles. Specifically, three blends included host-plant volatiles only, and four blends included *D. citri*-produced compounds in addition to plant volatiles. All seven blends of the second set were tested in Texas, and five blends were tested in Florida. Traps baited with the blends were checked and replaced weekly, and the number of *D. citri* captured on traps was counted. Results of Experiment Two are shown in FIGS. 5-6.

As can be seen, several of the blends tested resulted in a significant increase in the number of *D. citri* trapped as compared to un-baited control traps (FIGS. 3-6). Specifically, in Florida the experimental blends MS1, MS1L, MS1AL and MS1HC appeared most efficacious and promoted greater capture of *D. citri* on traps as compared with un-baited traps. Despite the lower numbers of *D. citri* populations in Texas during June and July of 2014, significant differences in the effectiveness of blends in luring adult *D. citri* were observed. Consistent with data obtained in Florida, traps baited with the experimental blends MS1A and MS1L captured significantly more *D. citri* than the un-baited ones. During the September-October 2014 study period in Texas, higher *D. citri* densities were recorded. Consequently, the number of *D. citri* captured dramatically increased, and marked differences were recorded in the performance of experimental blends tested. Traps baited with the MS1A, MS1L and MS1aL blends captured significantly more *D. citri* adults.

The disclosure above encompasses multiple distinct inventions with independent utility. While each of these inventions has been disclosed in a particular form, the specific embodiments disclosed and illustrated above are not to be considered in a limiting sense as numerous variations are possible. The subject matter of the inventions includes all novel and non-obvious combinations and subcombinations of the various elements, features, functions and/or properties disclosed above and inherent to those skilled in the art pertaining to such inventions. Where the disclosure or subsequently filed claims recite "a" element, "a first" element, or any such equivalent term, the disclosure or claims should be understood to incorporate one or more such elements, neither requiring nor excluding two or more such elements.

Applicant(s) reserves the right to submit claims directed to combinations and subcombinations of the disclosed inventions that are believed to be novel and non-obvious. Inventions embodied in other combinations and subcombinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

The invention claimed is:

1. An insect attractant comprising:
    a blend of volatile organic compounds, the blend comprising:
        alpha-phellandrene;
        beta-caryophyllene;
            wherein a ratio of alpha-phellandrene to beta-caryophyllene in the blend is 1:0.7 to 1:1; and
        at least one additional volatile organic compound.

2. The insect attractant of claim 1, wherein the at least one additional volatile organic compound is selected from the group consisting of: beta-phellandrene, gamma-terpinene, ocimene, and terpineol.

3. The insect attractant of claim 1, wherein the at least one additional volatile organic compound includes gamma-terpinene, and wherein the blend of volatile organic compounds comprises at least 5 wt. % gamma-terpinene.

4. The insect attractant of claim 1, wherein the at least one additional volatile organic compound includes beta-phellandrene, and wherein the blend of volatile organic compounds comprises at least 30 wt. % beta-phellandrene.

5. The insect attractant of claim 1, wherein the at least one additional volatile organic compound includes linalool.

6. The insect attractant of claim 5, wherein the blend of volatile organic compounds comprises at least 5 wt. % linalool.

7. An insect attractant comprising:
    a blend of volatile organic compounds, the blend comprising:
        15 to 60 wt. % alpha-phellandrene;
        10 to 50 wt. % beta-caryophyllene;
            wherein a ratio of alpha-phellandrene to beta-caryophyllene in the blend is 1:0.5 to 1:2; and
        at least one additional volatile organic compound.

8. The insect attractant of claim 7, wherein the at least one additional volatile organic compound is selected from the group consisting of: beta-phellandrene, gamma-terpinene, ocimene, and terpineol.

9. The insect attractant of claim 7, wherein the at least one additional volatile organic compound includes gamma-terpinene, wherein the blend of volatile organic compounds comprises at least 5 wt. % gamma-terpinene.

10. The insect attractant of claim 7, wherein the at least one additional volatile organic compound includes beta-phellandrene, and wherein the blend of volatile organic compounds comprises at least 30 wt. % beta-phellandrene.

11. The insect attractant of claim 7, wherein the blend of volatile organic compounds comprises at least 5 wt. % linalool.

12. An insect attractant comprising:
    a blend of volatile organic compounds, the blend comprising:
        15 to 60 wt. % alpha-phellandrene;
        10 to 50 wt. % beta-caryophyllene;
            wherein a ratio of alpha-phellandrene to beta-caryophyllene in the blend is 1:0.5 to 1:2; and
        at least 5 wt. % of one additional volatile organic compound selected from the group consisting of: beta-phellandrene, gamma-terpinene, ocimene, and terpineol.

13. The insect attractant of claim 7, wherein the ratio of alpha-phellandrene to beta-caryophyllene in the blend is 1:0.7 to 1:1.

* * * * *